US006538164B1

(12) United States Patent
Gallagher et al.

(10) Patent No.: US 6,538,164 B1
(45) Date of Patent: Mar. 25, 2003

(54) RECOVERY PROCESS FOR VOLATILE COMPOUNDS FROM SOLIDS IN AQUEOUS SOLUTION

(75) Inventors: F. Glenn Gallagher, Wilmington, DE (US); George Schurr, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 22 days.

(21) Appl. No.: 09/672,211

(22) Filed: Sep. 28, 2000

Related U.S. Application Data
(60) Provisional application No. 60/156,863, filed on Sep. 30, 1999.

(51) Int. Cl.[7] .............................................. C07C 27/26
(52) U.S. Cl. ..................... 568/871; 568/868; 568/869; 426/7; 209/133; 244/134; 560/248
(58) Field of Search ................. 568/871, 869, 568/868; 426/7; 209/133; 244/134; 560/248

(56) References Cited

U.S. PATENT DOCUMENTS

| 3,376,353 A | * | 4/1968 | Tate et al. |
| 4,497,838 A | | 2/1985 | Bonnell |
| 5,158,651 A | * | 10/1992 | Doerr et al. |
| 5,904,321 A | | 5/1999 | Cox et al. |

| 6,165,962 A | * | 12/2000 | Kaler et al. |

FOREIGN PATENT DOCUMENTS

GB 737570 * 9/1955

OTHER PUBLICATIONS

Perry's Chemical Engineering Handbook, 7th ed.: Perry, R. H. and Green, D. W., Eds; McGraw Hill: New York, 1997.
Handbook of Separation Techniques for Chemical Engineers, 2nd ed.: Schweitzer, P.A., Ed.; McGraw Hill: New York, 1988.
Biochemical Engineering and Biotechnology Handbook, 2nd ed.; Atkinson, B. and Mavituna, F., Eds.; Stockton Press: New York, 1991; Chapter 16, Figure 16.5.
Cook, Edward M. and DuMont, Harman D., McGraw Hill, Inc., New York, 1991.
Pikkov et al., (Khim. Prom (Moscow) 1973 49:11 (822–3).
Spray Drying Handbook, 5th ed.; Masters, K.: John Wiley & Sons: New York, 1991.

* cited by examiner

Primary Examiner—Deborah D. Carr (57) ABSTRACT

Volatile compounds may be economically recovered from solids present in aqueous solution by subjecting the solution to rapid separation where the volatilization occurs in a flash, spray, or fluid bed, or mechanically agitated dryers. Rapidly separating the solids from the volatile compound greatly simplifies the isolation of the volatile compounds from water. The methods have utility for fermentation processes, solids management, and recycling processes.

12 Claims, 5 Drawing Sheets

RECOVERY PROCESS FOR VOLATILE COMPOUNDS FROM SOLIDS IN AQUEOUS SOLUTION

This application claims the benefit of Provisional application Ser. No. 60/156,863, filed Sep. 30, 1999.

FIELD OF THE INVENTION

This invention relates to recovery of volatile compounds from solids present in an aqueous solution. Specifically, this invention relates to processes for recovering volatile compounds with normal boiling points at or above the boiling point of water from particulate or dissolved solids present in an aqueous solution.

BACKGROUND OF THE INVENTION

Over the years, there have been many technological developments in the field of aqueous waste stream processing. Environmental concerns have prompted advances in the treatment of organic compounds from aqueous waste streams as well as the substitution of organic solvents with water during synthesis. Wastewater treatment has focused on chemical or microbial reactions on aqueous waste streams to precipitate or destroy offensive compounds. For synthesis processes, the model of sequential separation of insoluble solids and water evaporation followed by purification of the organic compound has been widely practiced. Other techniques such as absorption, extraction, leaching, ion exchange, and bubble foam separation have been developed to improve operating efficiency and reduce cost during purification (*Perry's Chemical Engineering Handbook*, 7th ed.; Perry, R. H. and Green, D. W., Eds; McGraw Hill: New York, 1997 (hereinafter "Perry's"); *Handbook of separation Techniques for Chemical Engineers*, 2nd ed.; Schweitzer, P. A., Ed.; McGraw Hill: New York, 1988; *Biochemical Engineering and Biotechnology Handbook*, 2nd ed.; Atkinson, B. and Mavituna, F., Eds.; Stockton Press: New York, 1991; Chapter 16, FIG. 16.5).

Steam distillation or stripping has been traditionally used to purify temperature-sensitive volatile organic compounds. In steam stripping, water vapor (steam) is used to separate the volatile organic compound from less volatile compounds. The resulting products of steam stripping are aqueous heels containing less volatile compounds and volatile product with higher water content.

As described in Process Drying Practice (Cook, Edward M. and DuMont, Harman D., McGraw Hill, Inc., New York, 1991), techniques generally referred to as "drying" are routinely used to preserve solids from spoilage by removal of water, to reduce weight for shipping, to reduce weight or volume for packaging requirements, to make specific shapes or uniform mixtures, to recover solvents for reuse while drying solvent slurries, to separate noxious or toxic liquid(s) from solid(s), and to remove unwanted solid(s) and to recover the liquid.

The speed of drying influences solid formation and solid product quality. Rapid drying (i.e. rapid evaporation of volatile compounds from solids) has been found to be advantageous for temperature-sensitive materials as well as for controlling solid characteristics. These rapid drying techniques include flash drying, spray drying, fluidized bed drying, and mechanically-agitated drying where residence time is minutes or seconds.

Flash drying typically involves a very short exposure (a few seconds) of a slurry to a turbulent hot gas stream. Pikkov et al. (*Khim. Prom*. (Moscow) 1973, 49:11 (822–3)) describe a device for isolating glycerol from the liquid hydrogenolysis products of sucrose. The device contains a venturi nozzle through which superheated steam is injected and an inlet for the hydrogenolyate, which is fed at right angles to the steam jet.

Spray drying typically involves exposure of the slurry to hot gas in a vertical tower for tens of seconds. The slurry may be distributed into the tower with a variety of devices including spinning disk and nozzle atomizers (*Spray Drying Handbook*, 5th ed.; Masters, K.; John Wiley & Sons: New York, 1991; (hereinafter "Masters")). Spray drying has been extensively used in the chemical, food, pharmaceutical, and biochemical industries (Masters, supra, Part V). DD 155788 discloses a spray drying process to separate hydrocarbons and/or biological matter from a suspension of microbes grown on hydrocarbons and or other carbon sources with simultaneous cell decomposition, thus improving the biological value of the solid product. A suspension of microbes containing 17% solids, 3% hydrocarbon, and 80% water was heated to 175° C. at 9.5 atmospheres and then pressure was reduced to 1.1 atmospheres. The resulting product had higher solids content and lower content of extractable matter, fats and fatty acids, and hydrocarbons, steroids, and phosphatides.

Fluid bed drying of a slurry allows for increased contact between the slurry and the drying gas and/or heated surface by distributing the liquid feed source over the surface of an active, churning bed of relatively dry support solid. The drying bed is typically comprised of the recycled dried solids or an inert material. Volatile product residence time can be controlled from seconds to minutes by the relative mass flow of feeds to solids in the dryer (Perry, supra, Section 17).

Mechanically agitated drying describes a broad range of techniques and equipment where the slurry or solid is transported mechanically. Residence time of the volatile product can be from minutes to hours. Equipment in this category includes rotary hearth furnaces, tunnel dryers, conveyor belt dryers, rotary (kiln) dryers, rotating plate dryers, rotating (double cone) vacuum dryers, paddle dryers, ribbon dryers, as well as other mixing equipment with internal agitators to distribute slurry or solid while volatile products are removed with a stripping agent or vacuum (Perry, supra, Section 18).

The drying techniques described above have focused on solids management and the quality of the recovered solids. In contrast solvent recovery has been considered an environmental issue as part of solid drying, or as a technique to recycle organic solvents that are contaminated with suspended or dissolved solids. The solvent recovery techniques have addressed only non-aqueous systems.

Aqueous solutions containing volatile compounds and suspended or dissolved solids (such as the products of fermentation) are processed through solid/liquid separation systems such as filters or centrifuges to manage the suspended solids before recovery of the volatile compound from water. For volatile compounds with normal boiling points below water (such as ethanol), product is recovered directly from the fermentation broth using gas stripping, evaporation under vacuum, or steam distillation.

Solids management is often labor-intensive, may require specialized equipment, and is difficult to scale-up predictably. Traditional solids management techniques have the following deficiencies:

(1) Filtering to remove insoluble solids can be problematic, especially when the solids vary in type and composition or come from biological sources such as food processing or fermentation processes.

(2) To maximize the yield of recovered volatile product while minimizing the byproduct quantity, the isolated solid is typically washed with water. Washing can compromise refiltration of the solids and adds expense and handling concerns to the down-stream process.

(3) Evaporating water from volatile product in the presence of dissolved solids can be problematic due to precipitation of the solids, fouling of heat transfer surfaces, or undesirable degradation of the volatile product.

(4) Other techniques to manage the dissolved solids (such as membrane filtration, ion exchange, or adsorption) may increase the number of operations, add supplemental materials, generate additional waste streams to be managed, and increase the complexity of material movement. Each of these techniques adds to the cost of processing.

The prior art does not teach a reliable, efficient, and economical method for recovering volatile compounds with normal boiling points at or above that of water from particulate or dissolved solids present in aqueous solutions. The problem to be solved, therefore, is to overcome the difficulties of recovering volatile compounds from aqueous solutions containing solids in a reliable, efficient, and economical manner.

SUMMARY OF THE INVENTION

A process is provided for recovering volatile compounds from solids present in an aqueous solution comprising: (a) optionally pretreating the aqueous solution with at least one pretreatment, for instance, heating, concentrating, physically altering, or adding compounds to limit undesirable reactions or conditions or to promote favorable reactions or conditions. Such pretreatment additions include adjusting pH, temperature or pressure, introducing additives to coagulate solids or to provide a support for the solids, adding salts, adding alcohol, adding minerals, adding chelating compounds, and adding buffers. Additional steps include: (b) optionally using a stripping agent to facilitate vapor removal of the volatile compound(s); (c) removing volatile compounds from the aqueous solution with rapid separation ; and (d) isolating the volatile compound(s) from the solid product of the rapid separation (c). Rapid separation may be performed by 1) flash drying, spray drying, fluid bed drying, or mechanically agitated drying, 2) gas/solid separation, and 3) cooling. Isolating may be performed by condensing, distilling, or selective scrubbing. More particularly, the process may be used to recover 1,3-propanediol or glycerol from a fermentation broth.

BRIEF DESCRIPTION OF THE DRAWINGS

The instant invention is further elucidated with reference to the drawing, where.

DETAILED DESCRIPTION OF THE INVENTION

The present invention relates to a process for recovering volatile compounds with normal boiling points at or above that of water from particulate or dissolved solids present in aqueous solutions. The instant invention provides a solution to the deficiencies in the art by using rapid separation of the volatile compound from the insoluble and soluble solids, optionally aided by pretreating or a stripping agent. More specifically, the instant invention may be used to recover 1,3-propanediol from a fermentation broth using flash, spray, fluid bed, or mechanically agitated drying in combination with a gas/solid separation device, a cooler, and an optional isolation device, addition of an optional stripping agent, optional pretreating, and optional recycling of the stripping agent.

The current invention overcomes the deficiencies of the known methods as follows.

(1) Separation of volatile compounds from solids takes place in a vapor/solid phase instead of a liquid/solid phase. This is beneficial since the solids have been dried and have more consistent physical characteristics versus the wetted solids. In addition, the fluid going through the gas/solid separator is a gas having a more consistent low viscosity that is not influenced by solids content of the fluid;

(2) Rapid separation under appropriate conditions separates the volatile product from the solids with good yield and without the need for washing with water or other solvent to recover additional volatile product;

(3) The dissolved solids are precipitated before gas/solids separation and thus eliminated early in the process. Optional pretreatment of the aqueous solution and/or optional use of stripping agent(s) to facilitate vaporization further minimizes the influence of dissolved solids or other impurities on product quality; and (4) Concentrating solids handling into one unit operation that yields a dry solid significantly reduces the investment and operating costs of solids management.

The invention has utility where valuable volatile compounds are present in aqueous solutions containing dissolved and/or suspended solids. The aqueous solutions may originate during chemical or biological synthesis. The invention has utility where the volatile compound is a polyol produced in a fermentation process and the solid is a combination of microorganisms, proteins, and residual fermentation media components and substrate. The aqueous solution may also originate from recycling efforts such as polyol recycle from aircraft deicer or engine antifreeze applications, or solvent recycle from cleaning, degreasing, or stripping operations (microemulsion cleaning solution recovery), or chemical synthesis. Additionally, the invention has utility where the volatile compound is isolated from a natural plant or animal source in an aqueous solution as may be found in large livestock farming operations, or grain processing.

The term "aqueous solution" refers to a liquid in which the weight fraction of water is equal to or greater than the weight fraction of the volatile compound. A particular "aqueous solution" is that generated by fermentation processes.

The term "rapid separation" refers to separating volatile compound(s) from solid(s) in a period of less than about ten minutes. A rapid separation device is composed of three functions: 1) a vaporization section, 2) a gas/solid separation section, and 3) a cooling section. Vaporization can be achieved in a variety of devices traditionally used for rapid drying including flash, spray, mechanical agitation, and fluid bed drying. Gas/solid separation can be achieved in a variety of devices such as filters or cyclones (Perry, supra, Section 17). Cooling can be achieved in a variety of devices such as a heat exchanger, direct contact condenser, or indirect contact condenser (Perry, supra, Section 11).

The term "isolating" refers to recovering the volatile compound from the vapor or vapor/liquid mixture exiting the rapid separation device. Isolation can be achieved in a variety of devices such as gas/liquid separators, condensers, absorbers, distillation columns, or direct contact scrubbing devices (condensers or absorbers). To simplify equipment requirements, a single unit can be used to accomplish both the cooling required for rapid separation as well as the isolation of the volatile product.

The term "solid(s)" refers to any material that has an insufficient vapor pressure to be effectively vaporized (less than 10% mass loss) at operating temperature and pressure.

The term "volatile compound" refers to any material that has a normal boiling point at or above 100° C. and/or a sufficiently high vapor pressure to be separated from a solid as a vapor at operating temperature and pressure. Specific examples of volatile compounds include, but are not limited to, ethylene glycol, 1,2 propanediol, 1,3-propanediol, glycerol, succinic acid, and esters of aliphatic dicarboxylic acids.

The term "polyol" refers to an organic compound containing two or more hydroxyl groups. Specific examples of volatile polyol compounds include, but are not limited to, ethylene glycol, 1,2 propanediol, 1,3-propanediol, and glycerol.

The term "stripping agent" refers to a material that is a gas at operating temperature and pressure and that is able to carry away the volatile compound during the rapid drying process. Specific examples of stripping agents include, but are not limited to, nitrogen, air, carbon dioxide, the products of combustion, and other compounds with boiling points below the boiling point of the volatile compound (product) such as ammonia, methanol, or acetic acid. Use of a suitable stripping agent(s) yields dry solid without diluting the separated volatile compound (product) with additional water.

Pretreatment:

An optional pretreatment step may be used to modify the chemistry or physical characteristics of the feed composition resulting in improved operation and/or higher quality volatile product following rapid drying and recovery. Pretreatment of the starting aqueous stream can be advantageous to manage solid handling issues and minimize product degradation during rapid drying. The pretreatment may involve heating (exposing the feed to temperatures above 40° C.), concentrating (removal of some water and light components such as ethanol by evaporation, reverse osmosis, or other known techniques), physically manipulating or changing the materials (grinding particulates and filtering, or the use of temperature or pressure), adding compounds to limit undesirable reactions or conditions (for instance, adding base will limit dehydration of alcohol) or promote favorable reactions or conditions (for instance, adding methanol to form more volatile esters from carboxylic acids) before rapid drying. Examples of the adding of compounds include adjusting pH (with organic or mineral acids or bases), introducing additives to coagulate solids or to provide a support for the solids, adding salts (organic and/or mineral salts), adding alcohol, adding minerals (such as kaolin clay, filmed silica, or apatite), adding chelating compounds, and adding buffers.

Reactive Rapid Separation

In addition to the chemical changes that may occur during pretreatment, chemical changes may also occur during rapid separation. These changes may be especially valuable if the reaction product is more volatile than the starting volatile compound. These changes are due to the compounds added during pretreatment or due to interactions with the stripping agent. An appropriate choice of stripping agent(s) may retard undesirable chemistry from occurring during the rapid separation or promote desirable reactions during rapid separation. Alcohol, acids, bases, and inert materials as stripping agents may be useful in this fashion. For example, using methanol as the stripping agent may convert a carboxylic acid to a more volatile methyl ester. Similar benefits may result from using ammonia, carbon dioxide, or acetic acid as the stripping agent.

The cost of recycling the stripping agent or providing new stripping agent can be controlled by selecting operating conditions such that the concentration of volatile compound (s) in the stripping agent during the rapid drying is greater than about 1 weight percent and preferably greater than about 5 weight percent.

The term "reconditioning" as applied to the stripping agent recovered for recycling into the process refers to the series of steps to remove or neutralize undesirable byproducts that may be present in the stripping agent following the rapid separation and isolation of volatile compound(s). This reconditioning could be physical (for instance, to remove particulates with filtration or adsorption or absorption to remove volatile byproducts, or by changing temperature or pressure). This reconditioning could also be chemical in nature where a reaction occurs to convert the byproduct to a more desirable form or to aid with removal. Options for reconditioning are chosen based on the particular stripping agent and other characteristics of the materials used. These techniques are known to one of skill in the art.

EXAMPLES

The following examples illustrate certain embodiments of the instant invention. These particular embodiments of the invention do not limit the scope of the invention, which includes other embodiments envisioned in the specification.

In the examples which follow:

Volatile and non-volatile fractions of samples were determined by weight loss of solid or liquid sample in a vacuum oven with a slight nitrogen purge at 135° C. and 25" Hg vacuum over a 24 hour period.

Volatile compound content of solid samples was determined by combining one part solid with ten parts acetone and the mixture vortexed for five minutes. The suspension was filtered through a 2 μm PTFE syringe filter and the clear acetone solution analyzed by gas chromatography-flame ionization detection and gas chromatography-mass spectrometry.

Using the volatile compound content of the solid, percent volatile compound removal from the solid was calculated as follows. Since complete characterization of the solid was not performed, a precise determination of the extent of volatile compound removal could not be made. A conservative estimate is to assume only water and volatile compounds were removed and all other compounds in the feed material other than water and volatile compound remained in the solid. This assumption overestimates the mass of the solid remaining. Combined with the measured analysis of the volatile content of the solid, this overestimate of solids results in an overestimate of the volatile compound retained in the solid.

An estimate of the percent water and volatile compounds removed from the solids was calculated beginning on a basis of 100 grams of non-water materials contained in the feed. Water and volatile compounds were assumed to be removed while the weight of the other components are not changed. The percent water and volatile compounds removed was then calculated as $$100 \times \left( \frac{Starting\ Material\ Weight - Weight\ Remaining\ with\ Solids}{Starting\ Material\ Weight} \right)$$

The following sample calculation for a fermentation solution is presented for clarification.

| Starting Material Composition Concentration | % of Non Water Components | Grams/100 g |
|---|---|---|
| 60 g/L 1,3-propanediol | 40.8% | 40.8 |
| 70 g/L dry cells and medium component | 47.6% | 47.6 |
| 17 g/L glycerol | 11.6% | 11.6 |
| 147 g/L total material | 100% | 100 g |

Analysis of the resulting solid showed that it contained 7% 1,3-propanediol and 2.8% glycerol. Assuming only 1,3-propanediol and glycerol are liberated, the composition of solid in grams is:

| 1,3-propanediol | 0.07X |
| Dry cells and medium components | 47.6 |
| Glycerol | 0.028X |
| Total | X where X represents total weight of solid |

X=0.07X+47.6+0.028X

X=52.77

1,3-propanediol content is 3.7g and removal is $$\left( \frac{40.8 - 3.7}{40.8} \right) \times 100 = 90.9\%\ or\ in\ excess\ of\ 90\%.$$

Glycerol content is 1.48g and removal is $$\left( \frac{11.6 - 1.48}{11.6} \right) \times 100 = 87.2\%\ or\ in\ excess\ of\ 85\%.$$

The meaning of abbreviations is as follows: "sec" means second(s), "min" means minute(s), "h" means hour(s), "d" means day(s), "$\mu$L" means microliter(s), "mL" means milliliter(s), "L" means liter(s), "mM" means millimolar, "M" means molar, "mmol" means millimole(s), "g" means gram(s), "kg" means kilogram(s), "lb" means pound(s) and "ft" means feet.

Example 1

Rapid separation of volatile compound from aqueous solution containing solids.

This example demonstrates that rapid separation can efficiently remove volatile compounds (VC) from aqueous solution (AS) containing solids (S).

An aqueous solution (AS) containing greater than or equal to 1% volatile compound and greater than or equal to 1% solid is fed into a rapid separation device (1.2) consisting of three sections: a vaporization section (1.2A), a gas/solid separation section (1.2B), and a cooling section (1.2C). (See FIG. 1).

Figure 1:
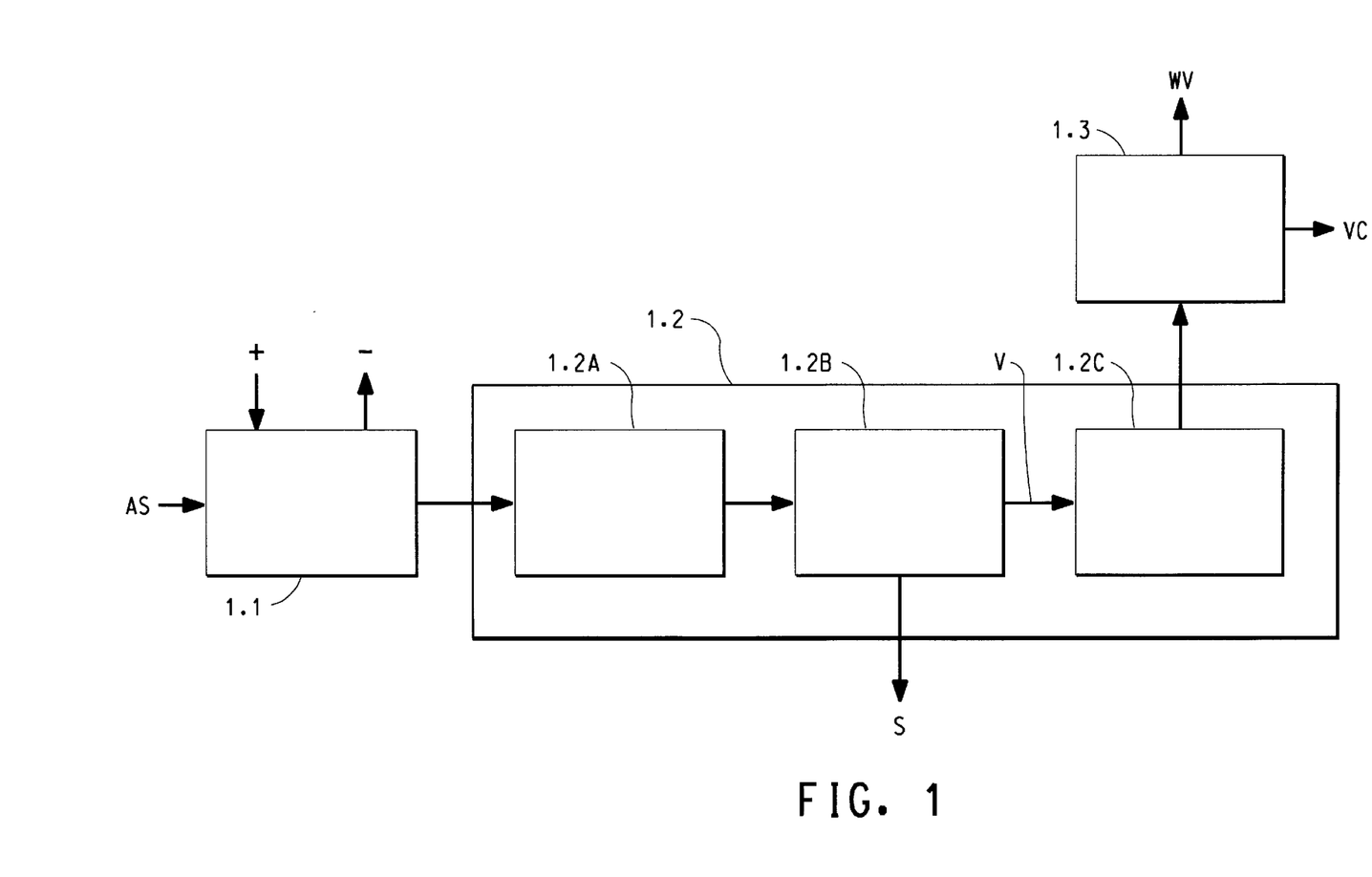
FIG. 1 illustrates a rapid separation process used in Examples 1–3.

In the vaporization section (1.2A), the fed aqueous solution (AS) is subjected to sufficient temperature and absolute pressure to vaporize the volatile compound (VC) as well as the water. The heat of vaporization is provided either by the sensible heat in the fed material, by thermal heat transfer into the vaporization section, and/or by alternate energy sources into the vaporization section (such as microwaves).

In the gas/solid separation section (1.2B), the solid (S) and vapor (V) are separated in a manner so that the resulting solid (S) contains only small amounts of the volatile compound (VC) fed. The temperature and absolute pressure in the gas/solid separation section (1.2B) must be maintained to avoid significant condensation of the volatile compound (VC).

In the cooling section (1 .2C), the temperature of the vapor is reduced to prevent undesirable reactions. The residence time in the rapid separation device (1.2) from vaporization to cooling is less than or equal to 10 minutes. The results expected for three test conditions are summarized in Table 1.

TABLE 1

| | | % of Volatile Compound Fed | | % of Solid Fed | |
|---|---|---|---|---|---|
| Test | Vaporized | In Solid | In Cooler Exit | In Solid | In Cooler Exit |
| 1a | >/= 50 | <50 | >/= 50 | >/= 90 | <10 |
| 1b | >/= 80 | <20 | >/= 80 | >/= 90 | <10 |
| 1c | >/= 90 | <10 | >/= 90 | >/= 90 | <10 |

Example 2

Rapid separation of volatile compound from aqueous solution containing solids with gas/liquid separation This Example is similar to Example 1, except that following the cooling section a gas/liquid separation section (1.3) is added to separate the condensed volatile compound (VC) from water vapor (WV) (see FIG. 1). The gas/liquid separation (1.3) can occur as a separate unit or in combination with the cooling section (1.2C). The results expected for three test conditions are summarized in Table 2.

TABLE 2

| | | % Of Volatile Compound Fed | | % Of Solid Fed | |
|---|---|---|---|---|---|
| Test | Vaporized | In Solids | In Product | In Solid | In Product |
| 2a | >/= 50 | <50 | >/= 50 | >/= 90 | <10 |
| 2b | >/= 80 | <20 | >/= 80 | >/= 90 | <10 |
| 2c | >/= 90 | <10 | >/= 90 | >/= 90 | <10 |

Example 3

Rapid separation of volatile compound from aqueous solution containing solids with gas/liquid separation and pretreatment of the feeds This Example is similar to Example 2, except that the feed material is pretreated (1) (by addition (+) or removal (−) of material and/or change in physical state) to improve subsequent processing (See FIG. 1). The results expected for three test conditions are summarized in Table 3.

TABLE 3

| | % Of Volatile Compound Fed | | | % Of Solid Fed | |
|---|---|---|---|---|---|
| Test | Vaporized | In Solids | In Product | In Solid | In Product |
| 3a | >/= 50 | <50 | >/= 50 | >/= 90 | <10 |
| 3b | >/= 80 | <20 | >/= 80 | >/= 90 | <10 |
| 3c | >/= 90 | <10 | >/= 90 | >/= 90 | <10 |

Example 4

Rapid separation of volatile compound from aqueous solution containing solids with the aid of stripping agent.

Figure 2:
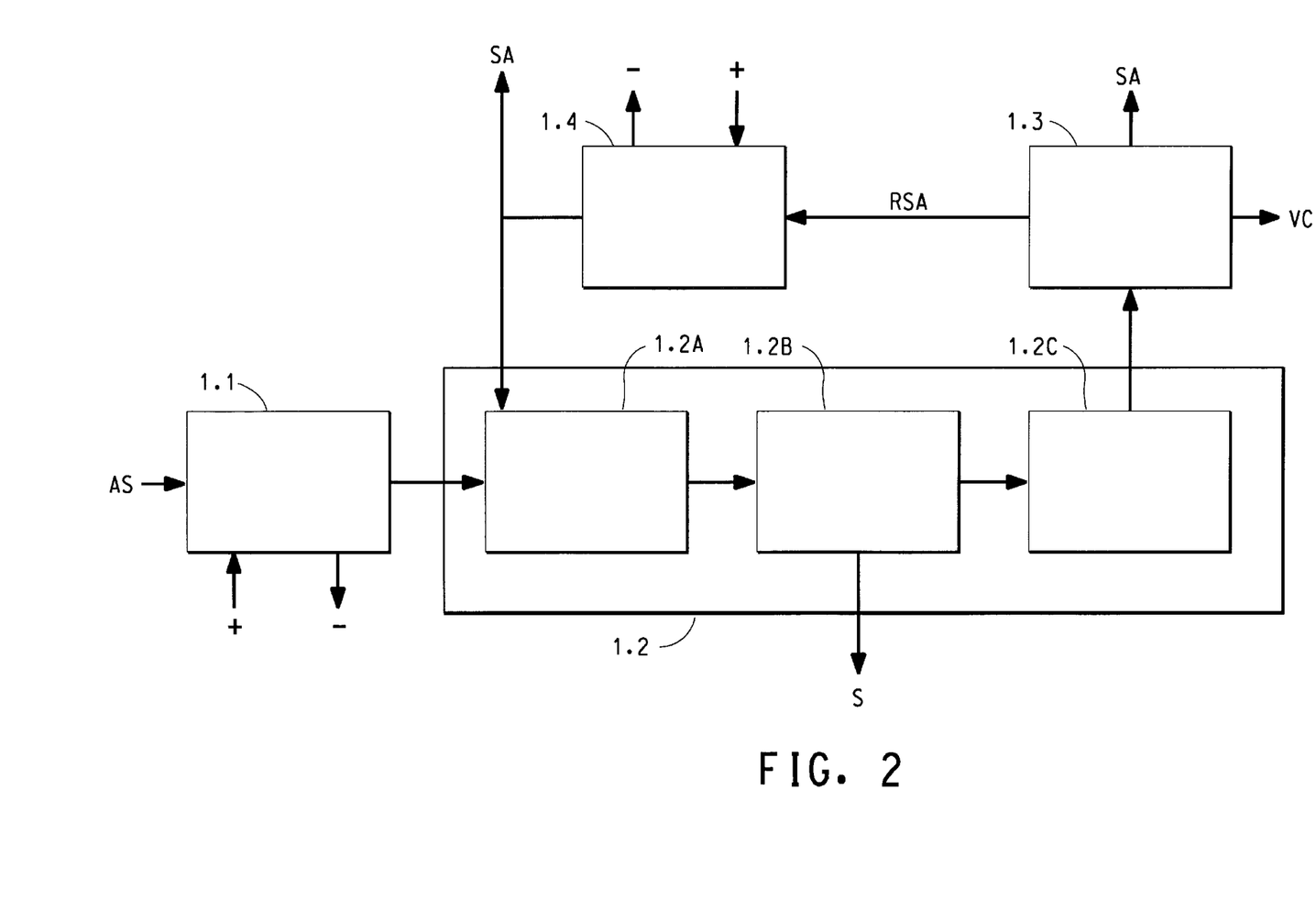
FIG. 2 illustrates a rapid separation process used in Examples 4–8.

This Example is similar to Example 1, except that a stripping agent (SA) (for instance, nitrogen), is added to the vaporization section (1.2A) (see FIG. 2). The stripping agent (SA) improves operability by lowering the temperature and/or raising the absolute pressure requirements to achieve vaporization in the vaporization section (1.2A). The stripping agent (SA) is preferably fed as a warm gas to provide some heat to the vaporizer (1.2A). The results expected for three test conditions are summarized in Table 4.

TABLE 4

| | % Of Volatile Compound Fed | | | % Of Solid Fed | |
|---|---|---|---|---|---|
| Test | Vaporized | In Solids | In Cooler Exit | In Solid | In Cooler Exit |
| 4a | >/= 50 | <50 | >/= 50 | >/= 90 | <10 |
| 4b | >/= 80 | <20 | >/= 80 | >/= 90 | <10 |
| 4c | >/= 90 | <10 | >/= 90 | >/= 90 | <10 |

Example 5

Rapid separation of volatile compound from aqueous solution containing solids with stripping agent and gas/liquid separation This Example is similar to Example 4, except that following the cooling section (1.2C) a gas/liquid separation section (1.3) is added to separate the condensed volatile compound (VC) from the stripping agent (SA) (see FIG. 2). The gas/liquid separation can occur in a separate unit (1.3) or in combination with the cooling section (1.2C). The results expected for three test conditions are summarized in Table 5.

TABLE 5

| | % Of Volatile Compound Fed | | | % Of Solid Fed | |
|---|---|---|---|---|---|
| Test | Vaporized | In Solids | In Product | In Solid | In Product |
| 5a | >/= 50 | <50 | >/= 50 | >/= 90 | <10 |
| 5b | >/= 80 | <20 | >/= 80 | >/= 90 | <10 |
| 5c | >/= 90 | <10 | >/= 90 | >/= 90 | <10 |

Example 6

Rapid separation of volatile compound from aqueous solution containing solids with a stripping agent. gas/liquid separation, and pretreatment of the feeds This Example is similar to Example 5, except that the feed material (AS) is pretreated by the addition (+) or removal (−) of material and/or change in physical state to improve subsequent processing (1.1) (see FIG. 2). The results expected for three test conditions are summarized in Table 6.

TABLE 6

| | % Of Volatile Compound Fed | | | % Of Solid Fed | |
|---|---|---|---|---|---|
| Test | Vaporized | In Solids | In product | In solid | In product |
| 6a | >/= 50 | <50 | >/= 50 | >/= 90 | <10 |
| 6b | >/= 80 | <20 | >/= 80 | >/= 90 | <10 |
| 6c | >/= 90 | <10 | >/= 90 | >/= 90 | <10 |

Example 7

Rapid separation of volatile compound from aqueous solution containing solids with stripping agent, gas/liquid separation and stripping agent recycle This Example is similar to Example 5, except that following the gas/liquid separation section (1.3) the stripping agent (SA) is recycled (1.4) to the vaporization section (1.2A) (see FIG. 2). As part of the recycle section (1.4) some gas is vented (−) while new stripping agent (SA) (+) is added. Some water vapor and other low boiling compounds may leave with the vented gas depending on the gas temperature.

In addition, the recycled stripping agent (RSA) may require reconditioning (for instance, re-heating for improved volatilization performance or physical or chemical treatment to remove undesirable compounds in the recycled stripping agent). The results expected for three test conditions are summarized in Table 7.

TABLE 7

| | % Of Volatile Compound Fed | | | % Of Solid Fed | |
|---|---|---|---|---|---|
| Test | Vaporized | In Solids | In product | In solid | In product |
| 7a | >/= 50 | <50 | >/= 50 | >/= 90 | <10 |
| 7b | >/= 80 | <20 | >/= 80 | >/= 90 | <10 |
| 7c | >/= 90 | <10 | >/= 90 | >/= 90 | <10 |

Example 8

Rapid separation of volatile compound from aqueous solution containing solids with a stripping agent gas/liquid separation, stripping gas recycle, and pretreatment of the feeds This Example is similar to Example 7, except that the feed material (AS) is pretreated (1.1) (by an addition or removal of compounds and/or change in physical state) to improve subsequent processing (see FIG. 2). The results expected for three test conditions are summarized in Table 8.

TABLE 8

| | % Of Volatile Compound Fed | | | % Of Solid Fed | |
|---|---|---|---|---|---|
| Test | Vaporized | In Solids | In product | In solid | In product |
| 8a | >/= 50 | <50 | >/= 50 | >/= 90 | <10 |
| 8b | >/= 80 | <20 | >/= 80 | >/= 90 | <10 |
| 8c | >/= 90 | <10 | >/= 90 | >/= 90 | <10 |

Example 9

This Example is similar to Example 7, except that the stripping gas is the combustion product of methane or natural gas with air. Combustion conditions and recycled stripping agent rates are adjusted so that the oxygen content in the vaporization section (1.2A) is at or below 4%. This self-inertizing approach is described in Masters'supra, at page 51. The results expected for three test conditions are summarized in Table 9.

TABLE 9

| | % Of Volatile Compound Fed | | | % Of Solid Fed | |
|---|---|---|---|---|---|
| Test | Vaporized | In Solids | In Product | In Solid | In Product |
| 9a | >/= 50 | <50 | >/= 50 | >/= 90 | <10 |
| 9b | >/= 80 | <20 | >/= 80 | >/= 90 | <10 |
| 9c | >/= 90 | <10 | >/= 90 | >/= 90 | <10 |

Example 10

This Example is similar to Example 6 with the following changes. The aqueous solution is derived from fermentation with ethanol as the primary product and the volatile compound is glycerol. The fermentation broth is pretreated by vacuum or steam distillation to remove the ethanol. The resulting aqueous solution containing microbes, residual media and substrate components, and glycerol is further pretreated in an evaporator to remove water and concentrate the glycerol to at or above 5 weight percent. The concentrate is fed into a rapid separation device composed of a spray drying chamber for vaporization, a bag house filter to separate solids from the vapor, and a direct contact spray condenser with recirculating condensate to cool the gas and separate the liquid from the gas (see Perry's supra section 11). Hot inert gas is fed into the spray-drying chamber (SDC) at 300° C. and 5 PSIG as a stripping agent and as a source of heat for volatilization. The mass ratio of hot gas to liquid feed is adjusted so that at least 80% of the glycerol is vaporized and exits the spray-drying chamber as a vapor. The temperature of the bag house filter is maintained sufficiently hot to prevent glycerol condensation. The operating temperature of the direct contact spray condenser is adjusted to condense at least 95% of the glycerol present while permitting water to be vented with the stripping gas.

Example 11

This Example is similar to Example 10 with the following changes. The aqueous solution is derived from a fermentation with calcium succinate as the primary product. The fermentation broth is pretreated by acidification with sulfuric acid. The resulting aqueous solution containing microbes, residual media and substrate components, calcium sulfate, and succinic acid is further pretreated in an evaporator to remove water and to concentrate the succinic acid at or above 10 weight percent. The concentrate is fed into a rapid separation device similar to that in Example 10. Hot inert gas is fed into the spray-drying chamber at 300° C. and 5 PSIG as a stripping agent and as a source of heat for volatilization. The mass ratio of hot gas to liquid feed is adjusted so that 80% of the succinic acid volatilizes and exits the spray-drying chamber as a vapor. The temperature of the bag house filter is maintained sufficiently hot to prevent succinic acid condensation. The operating temperature of the direct contact spray condenser is adjusted to condense at least 95% of the succinic acid present while permitting water to be vented with the stripping gas.

Example 12

Flash Drying Fermentation Broth

This Example demonstrated that flash drying can efficiently remove volatile compounds from fermentation broth.

Figure 3:
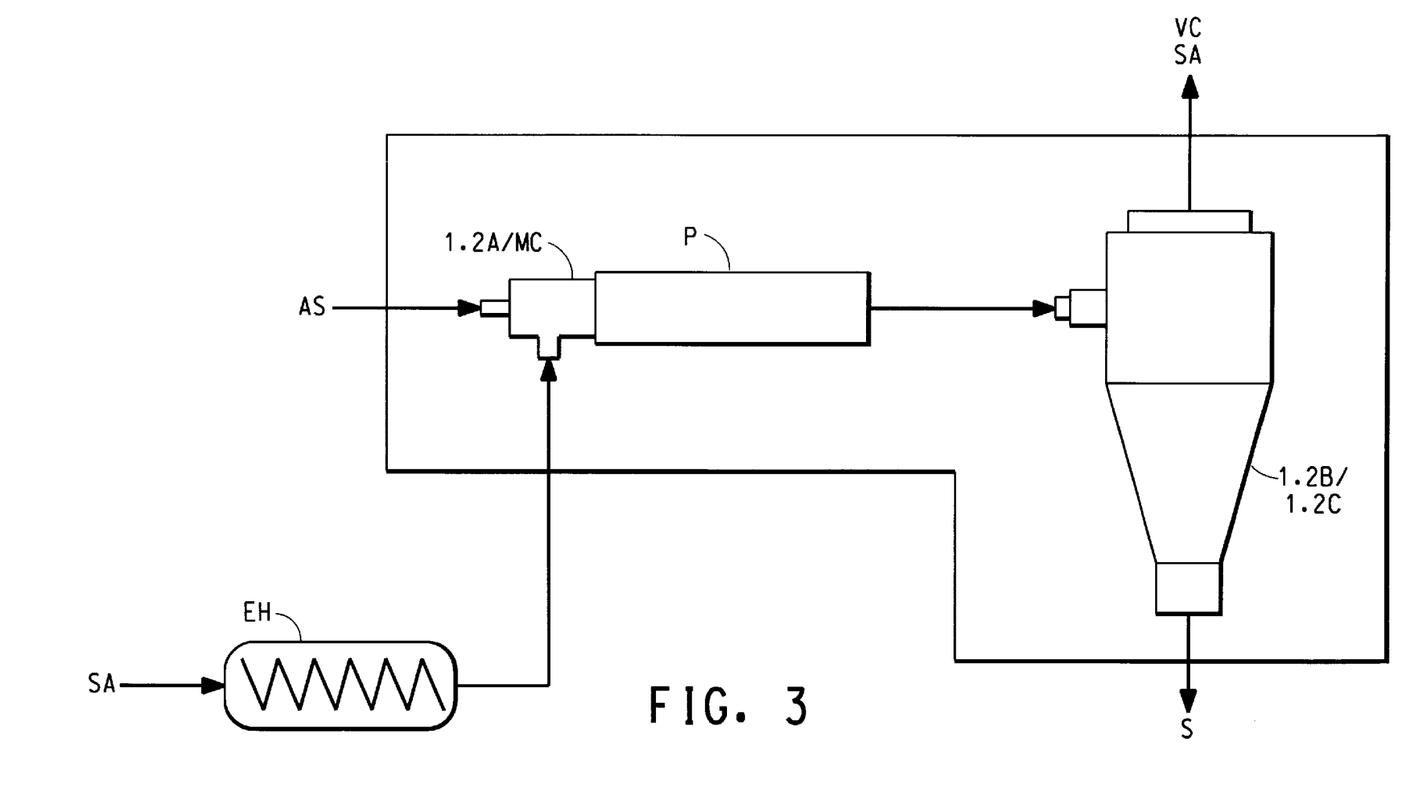
FIG. 3 illustrates a flash drying apparatus used in Example 12.

A fermentation broth or aqueous solution (AS) containing 70 g/l dry cells and non-volatile medium components, 60 g/L 1,3-propanediol, and 17 g/L glycerol was fed through a flash drying apparatus (see FIG. 3). The instant flash drying apparatus (FIG. 3) consisted of a stripping agent (SA) supply with an electric heater (EH), a peristaltic tube pump for feeding slurries, a mixing chamber (1.2A/MC) constructed from a 0.368" divergent nozzle outfitted with a concentric 0.25 " stainless steel tube feeding a 1" pipe (P) 10 inches long, and a 5" cyclone (1.2B/1.2C). Dry nitrogen was fed at 295°C. into the 0.368" divergent nozzle while 80 g/min of fermentation broth (AS) was fed from a water ice-cooled container. The stripping agent (SA) and volatile compound (VC) exit temperature from the cyclone was 137°C. The residence time of the volatile compound from volatilization to exit of the cyclone was less than 1 second.

At the conclusion of the 6 min, 41 sec test, gas feeds were terminated and the equipment disassembled to recover solids.

A light brown dusty powder was collected from the 5" cyclone and analyzed. The solids (S) contained 7% 1,3-propanediol and 2.8% glycerol. A conservative assumption that only water, 1,3-propanediol, and glycerol were evaporated, suggests that in excess of 90% of the 1,3-propanediol and in excess of 85% of the glycerol were removed during the flash drying process.

Example 13

Fluidized Particulate Bed Driving Fermentation Broth

This Example demonstrated that fluidized particulate bed drying can effectively remove volatile organic compounds from fermentation broth.

A fermentation broth (AS) with a nominal composition of 57 g/L dry cells and non-volatile medium components, 57.3 g/L 1,3-propanediol, and 6.4 g/L glycerol was pretreated by atmospheric concentration. 7.9 Kg of broth was charged to a 15 gallon stainless steel agitated vessel equipped with a jacketed heating system and a vent line with a total condenser. The temperature was gradually raised to approximately 96° C. until condensate was collected. The concentration was performed in two stages. In the first stage, 2.6 kg of condensate was collected and analyzed by gas chromatography to contain pure water. The second condensate collected was 877 grams and was analyzed by gas chromatography to contain water and 0.034 g/L 1,3-propanediol. There was no evidence of glycerol. The resulting 4.4 kg of concentrate was stored at 5° C. for further processing.

The concentrate was dried in a venturi-type fluid bed dryer using a solid support. A venturi-type fluid bed was constructed (see Perry's supra, Section 17, page 3). The volatilizing agent (superheated air) was supplied to the unit in a bottom reservoir, which was flanged to a small cross section of a conical stainless steel section, which was in turn flanged to a short 12-inch diameter cylindrical section. The rectifying bed of solid support occupied the lower 7–8" of the conical section and was supported above the gas feed section by a perforated plate and steel wool. $ZrO_2$ milling media (0.8 mm to 1.2 mm grade) was used as the solid support. The feed concentrate slurry (AS) was metered by a peristaltic tube pump and discharged through a 0.25" stainless steel tube into the rectifying bed approximately three inches above the stripping agent (SA) feed zone. The vapor and entrained solids exited the contact chamber through a 2" diameter port that fed into a 5" cyclone. The residence time of the volatile compound from volatilization to exit of the cyclone was less than 2 seconds.

The stripping agent was maintained at 197 to 199° C., while the vapor space above the churning bed ranged from 132 to 137° C. Aqueous solution (AS) feed was 28.4 g/min. Test conditions were maintained for 1 h with no apparent aggregation of the bed material.

Solid residue was collected from the 5" cyclone and analyzed. The solids contained 1.8% 1,3-propanediol and 4.3% glycerol. A conservative assumption that only water, 1,3-propanediol, and glycerol were evaporated suggests in excess of 98% of the 1,3-propanediol and in excess of 60% of the glycerol were removed during the flash drying process.

Examples 14, 15, and 16

Examples 14, 15, and 16 (set out in detail below) were conducted in a spray drying apparatus (1.2) described above (Masters, supra) and shown in FIG. 4. Vaporization (1.2A) occurred in a Niro 30" contact chamber from a standard Niro "Mobile Minor" laboratory spray drying unit. The atomizer (1.2AA) was a pneumatic-driven, centrifugal type "M-02/B" provided with the Mobile Minor, portable unit package. Nitrogen was used as a stripping agent (SA) to drive the atomizer. The bag house filter (1.2B) was a MikroPul "Mikro-D Pulsaire Collector" with singed Nomex®, non-woven filters with 7.5 $ft^2$ of available filter area. The condenser (1.2C) was a jacketed stainless steel pipe with an internal cooling coil and integral gas/liquid separation (1.3) section. The residence time for the volatile compound from vaporization to cooling was less than 1 minute.

Example 14

Spray Driving Fermentation Broth

This Example demonstrated that spray drying can efficiently remove volatile organic products from fermentation broth containing non-volatile solids.

Figure 4:
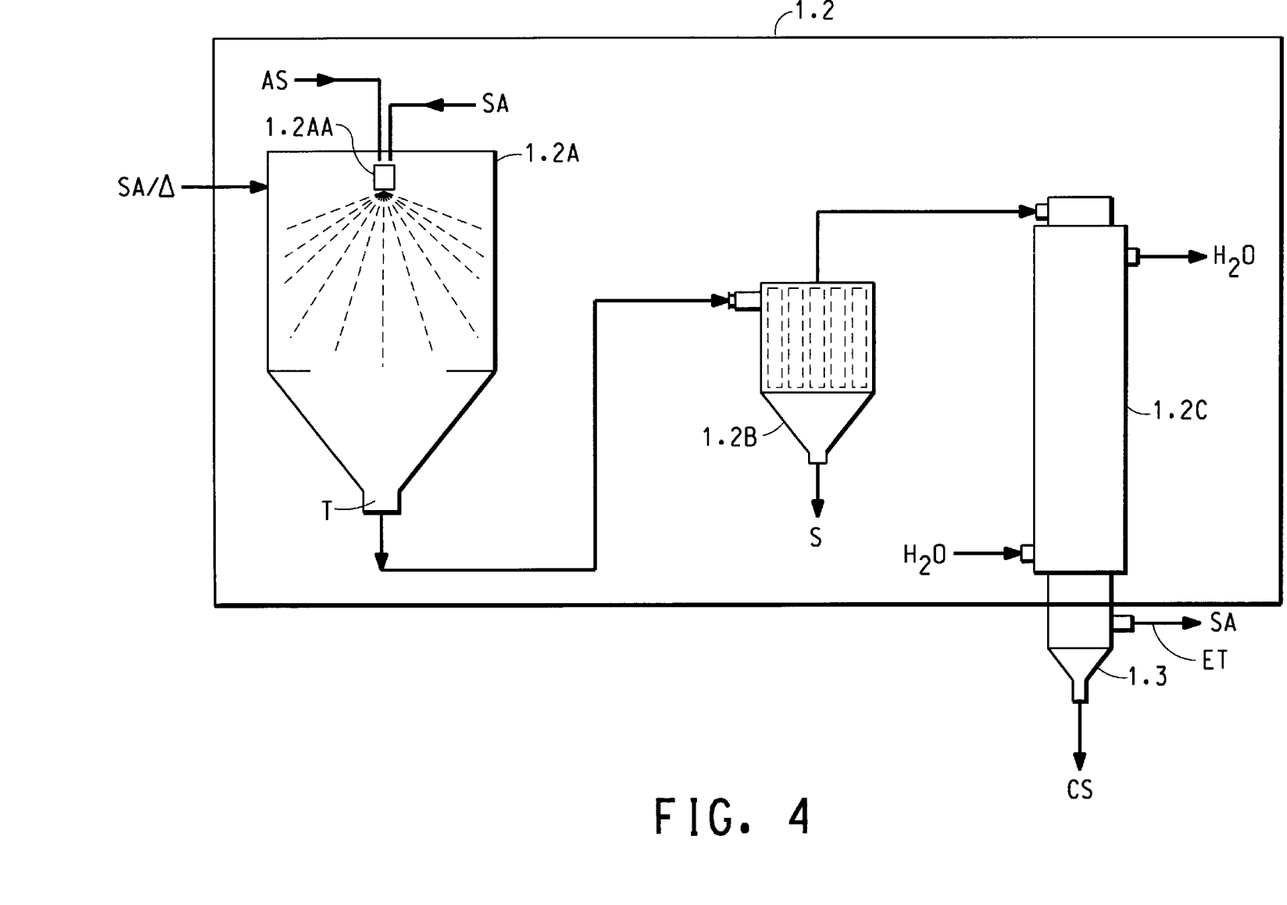
FIG. 4 shows a schematic of a generic spray drying apparatus used in Examples 14–16.

A fermentation broth (AS) with a nominal composition of 40 g/L dry cells and non-volatile medium components, 68 g/L 1,3-propanediol, and 11 g/L glycerol was fed through the spray drying apparatus. Nitrogen (SA/Δ) was heated to at least 225° C. and fed to the contact chamber (1.2A) at the equipment-designed flow rate. Fermentation broth (AS) was fed to the atomizer (1.2AA) at a flow rate to achieve a gas discharge temperature (T) for the contact chamber above 160° C. The bag house filter (1.2B) was maintained hot to limit condensation in the bag house filter. The condensate (1.2C/1.3) exit temperature (ET) was at or below 70° C.

Solid samples (S) were collected from the bag house filter (1.2B) for an analysis and demonstrated at least 99% of the 1,3-propanediol and at least 99% of the glycerol was effectively removed with the gas. Condensate samples (CS) collected from the condenser for non-volatiles analysis demonstrate at least 99% removal of the non-volatile solids.

Example 15

Concentration of Fermentation Broth Followed by Spray Drying Fermentation Broth

This Example was similar to Example 14, differing in the addition of a concentration pretreatment step.

A fermentation broth (AS) with a nominal composition of 42 g/L dry cells and non-volatile medium components, 71 g/L 1,3-propanediol, and 6 g/L glycerol was charged to a stainless steel agitated vessel equipped with a jacketed heating system, a vent line with a total condenser and a vacuum source. The vessel temperature was gradually raised to about 55° C. while the pressure was reduced to about 26 in Hg until condensate was collected. Temperature was maintained until 50% of the mass of the original charge was collected as condensate. The condensate was analyzed by HPLC and determined to be water with only trace quantities of 1,3 propanediol. The resulting concentrate was stored at 5° C. for further processing.

The concentrate was fed through the spray drying apparatus (1.2) with a hot nitrogen (SA/Δ) feed temperature of 320° C. and a contact chamber exit gas temperature (T) of 160° C. Solid samples (S) collected from the bag house filter (1.2B) demonstrate that at least 98% of the 1,3-propanediol and at least 90% of the glycerol were effectively removed with the gas. Condensate samples (CS) collected from the condenser (1.2C/1.3) for non-volatile analysis demonstrate at least 99% removal of the non-volatile solids.

Example 16

Pretreatments with Disodium Phosphate Followed by Concentration of Fermentation Broth. and Then Spra Driving Fermentation Broth This Example was similar to Example 15 with the addition of a disodium phosphate pretreatment.

A fermentation broth (AS) with a nominal composition of 60 g/L dry cells and non-volatile medium components, 110 g/L 1,3-propanediol, and 13 g/L glycerol was agitated in a vessel while 3g/L disodium phosphate was added to adjust the pH to above 7.0. The stainless steel agitated vessel was equipped with a jacketed heating system, a vent line with a total condenser, and a vacuum source. The vessel temperature was gradually raised to about 55° C. while the pressure was reduced to about 26 in Hg until condensate was collected. Temperature was maintained until 50% of the mass of the original charge was collected as condensate. The condensate was analyzed by HPLC and determined to be water with only trace quantities of 1,3 propanediol. The resulting concentrate was stored at 5° C. for further processing.

The concentrate was fed through the spray drying apparatus (1.2) with a nitrogen feed (SA/Δ) temperature of 316° C. and a contact chamber exit gas temperature (T) of 150° C. Solid samples (S) were collected from the bag house filter (1.2B) for an analysis and demonstrate at least 99% of the 1,3-propanediol and at least 99% of the glycerol were effectively removed with the gas. Condensate samples (CS) collected from the condenser (1.2C/1.3) for analysis demonstrate at least 99% removal of the non-volatile solids.

Examples 17–22

Figure 5:
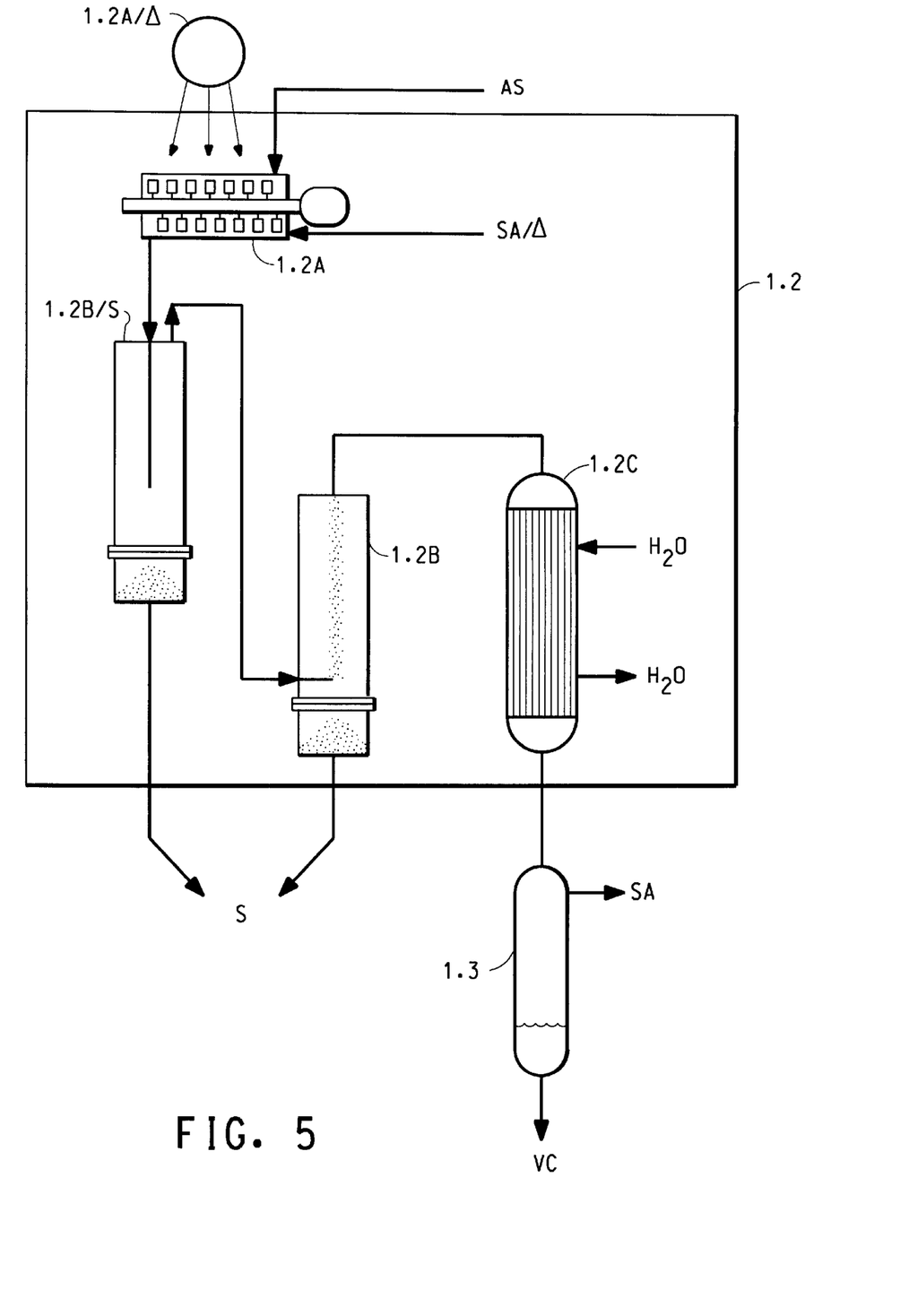
FIG. 5 shows a schematic of an indirectly heated, mechanically agitated dryer used in various embodiments in Examples 17–22.

Examples 17–22 (set out in detail below) were conducted using a rapid separation device (1.2) consisting of a mechanically agitated dryer of the indirectly heated variety (1.2A), a bag house filter (1.2B), and an indirect contact condenser (1.2C). FIG. 5 illustrates this. In the agitated dryer, the material to be dried (AS) was fed to one end of a horizontal hollow vessel (1.2A). A shaft, possessing multiple paddles, was used to mix the solids formed and to keep the inner surface of the vessel clean. Heat (1.2A/$\Delta$) was transferred through the outer shell of the vessel to provide the heat of evaporation for the materials being vaporized. Additional heat was added to the vessel by preheating the nitrogen fed (SA/$\Delta$). For cases where the mixture being fed was a pumpable liquid, the unit was operated under vacuum. Vacuum operation reduced or eliminated the need for a stripping agent. The gas and vapors leaving the dryer were passed through a gas/solid gravity settling separator (1.2B/S) and a bag house filter (1.2B) to separate solids before being cooled in an indirect contact condenser (1.2C). The resulting gas/liquid mixture was then transferred to a gas/liquid separator (1.3) to recover volatile product condensate.

Example 17

Mechanically Agitated, Indirectly Heated Recovery of Polyol

This Example demonstrates the ability of a mechanically agitated dryer using indirect heating of the drying mixture under vacuum to recover 1,3-propanediol from a vacuum-concentrated fermentation broth.

This Example was similar to Example 15 except that volatilization occurs in a mechanically agitated, indirectly heated dryer unit. This feed material was pretreated similar to Example 15 by vacuum evaporation to remove 50% of the mass. The concentrate was analyzed and determined to contain 22.85% 1,3-propanediol, 2.29% glycerol, and 12.7% solids (dry cells and non-volatile medium components).

The unit was operated at 7.3 psia with exit temperature of the agitated dryer maintained at 130° C. Concentrate (AS) was fed to the unit at 1.45 lb/h. Nitrogen (SA/$\Delta$) was co-fed to the unit at 19.2 lb/hr and 150° C. The agitator on the dryer was operated at 1,700 RPM.

Analysis of the solids demonstrated at least 96% of the 1,3-propanediol and at least 87% of the glycol were effectively removed from the solids. The condensate was analyzed and determined to contain non-detectable quantities of solids.

Example 18

Mechanically Anitated, Indirectly Heated Recovery of a Polvol

This Example demonstrates the ability of a mechanically agitated dryer using indirect heating of the drying mixture under vacuum to recover 1,3-propanediol from a fermentation broth.

This Example was similar to Example 14 except that volatilization occurs in a mechanically agitated, indirectly heated dryer unit. The fermentation broth (AS) fed was analyzed and determined to contain 6.77% 1,3 propanediol, 1.1% glycerol, and 2.9% solids (dry cells and non-volatile medium components).

The unit was operated at 7.3 psia with exit temperature of the agitated dryer maintained at 139° C. Broth (AS) was fed to the unit at 1.64 lb/h. Nitrogen (SA/$\Delta$) was co-fed to the unit at 19.2 lb/hr and 150° C. The agitator on the dryer was operated at 1,700 RPM.

Analysis of the solids demonstrated that at least 99% of the 1,3-propanediol and at least 70% of the glycerol were effectively removed from the solids.

The condensate was analyzed and determined to contain non-detectable quantities of solids.

Example 19

Mechanically Agitated Indirectly Heated Recovery of a Polyol

This Example demonstrates the ability of a mechanically agitated dryer using indirect heating of the drying mixture under vacuum to recover 1,3-propanediol from a concentrated fermentation broth pretreated with $CaCO_3$.

This Example was similar to Example 17 but with the addition of 1% $CaCO_3$ to the concentrate prior to volatilization. The $CaCO_3$ treated fermentation broth concentrate was analyzed and determined to contain 21.7% 1,3-propanediol, 2.18% glycerol, and 13.2% solids ($CaCO_3$, dry cells and non-volatile medium components).

The unit was operated at 7.3 psia with exit temperature of the agitated dryer maintained at 133.5° C. Concentrated $CaCO_3$ treated broth (AS) was fed to the unit at 2.25 lb/h. Nitrogen (SA/$\Delta$) was co-fed to the unit at 19.2 lb/h and 149° C. The agitator on the dryer was operated at 1,700 RPM.

Analysis of the solids demonstrated at least 99% of the 1,3-propanediol and at least 89% of the glycerol were effectively removed from the solids.

The condensate was analyzed and determined to contain non-detectable quantities of solids.

Example 20

Mechanically Agitated, Indirectly Heated Recovery of a Deicing Mixture

This Example demonstrates the ability of a mechanically agitated dryer using indirect heating of the drying mixture under vacuum to recover 1,2-propanediol from a mixture approximating recovered aircraft deicing fluid. Standard aircraft deicing fluid was obtained from the Wilmington Airport (DE) and combined with an equal volume of water and 1.2% potassium acetate to approximate the aqueous solution (AS) that might be recovered from an aircraft deicing operation. The resulting mixture was analyzed and determined to contain 22% 1,2-propanediol and 3.7% solids (potassium acetate and non-volatile components in the deicing fluid).

The unit was operated at 7.3 psia with exit temperature of the agitated dryer maintained at 145° C. The synthetic aqueous solution (AS) was fed to the unit at 2.0 lb/h. Nitrogen (SA/$\Delta$) was co-fed to the unit at 19.0 lb/hr and 149° C. The agitator on the dryer was operated at 1,700 RPM. A fine granular solid was recovered from the unit.

Analysis of the solids demonstrated at least 97% of the 1,2-propanediol was effectively removed from the solids. The condensate was analyzed and determined to contain non-detectable quantities of solids.

Example 21

Mechanically Agitated. Indirectly Heated Recovery of an Antifreeze Solution

This Example demonstrates the ability of a mechanically agitated dryer using indirect heating of the drying mixture under vacuum to recover ethylene glycol from a mixture approximating recovered automotive antifreeze. Automotive antifreeze (Proline®) was combined with an equal volume of water and 1.2% residual solids (from a broth spray drying experiment similar to Example 15) to approximate the aqueous solution that might be recovered from an automobile cooling system. The resulting mixture was analyzed and determined to contain 32% ethylene glycol and 2.3% solids (residual solids and non-volatile components in the antifreeze.

The unit was operated at 7.3 psia with exit temperature of the agitated dryer maintained at 131° C. The synthetic aqueous solution (AS) was fed to the unit at 1.6 lb/h. Nitrogen (SA/Δ) was co-fed to the unit at 19.0 lb/h and 149° C. The agitator on the dryer was operated at 1,700 RPM. A fine granular solid was recovered from the unit.

Analysis of the solids demonstrated that at least 95% of the ethylene glycol was effectively removed from the solids.

The condensate was analyzed and determined to contain non-detectable quantities of solids.

Example 22

Dibasic Ester (DBE) Emulsion Recovery

This Example demonstrates the ability of a mechanically agitated dryer using indirect heating of the drying mixture under vacuum to recover dimethyl esters (a DBE) from a microemulsion cleaning composition described in U.S. application Ser. No. 09/050,307 (Kaler et al).

A microemulsion cleaning solution (AS) was prepared by combining water with dimethyl esters of adipic, glutaric, and succinic acids, a high boiling point anionic surfactant (sodium bis(2-ethylhexyl) sulfosuccinate), and a diol (neopentyl glycol). The microemulsion was analyzed and determined to contain 34.5% volatile components and 11.6% non-volatile solids (the surfactant).

The unit was operated at 7.3 psia with the exit temperature of the agitated dryer maintained at 149° C. Synthetic aqueous solution (AS) was fed to the unit at 2.0 lb/h. Nitrogen (SA/Δ) was co-fed to the unit at 19.0 lb/h and 149° C. The agitator on the dryer was operated at 1,700 RPM.

At the conclusion of the run, most of the solids were observed inside the agitated dryer as a tightly adherent layer of viscous liquid. Analysis of this viscous liquid using the solids analysis established a non-detectable quantity of volatile compounds. In this example, the gas/solid separation (1.2B) occurred in the mechanically agitated dryer.

The condensate was analyzed and determined to contain non-detectable quantities of solids as well as volatile compounds such as dimethyl esters of adipic, glutaric, and succinic acids and neopentyl glycol.

What is claimed is:

1. A process for recovering volatile compounds from solids present in an aqueous solution comprising:
    (a) optionally pretreating the aqueous solution;
    (b) mixing a stripping agent with the aqueous solution;
    (c) separating volatile compounds from solids present in the aqueous solution by rapid separation; and
    (d) optionally isolating the volatile compound from the vapor product of step (c).

2. The process of claim 1 wherein pretreating comprises adding compounds to limit undesirable reactions or conditions or to promote desirable reactions or conditions, heating, concentrating, or altering physically.

3. The process of claim 2 wherein adding compounds to limit undesirable reactions or conditions or to promote desirable reactions or conditions comprises at least one of adjusting pH, adding additives to coagulate solids or provide a support for solids, adding salts, adding alcohol, adding minerals, adding chelating compounds, or adding buffers.

4. The process of claim 1 wherein separating volatile compounds from the solids present in the aqueous solution by rapid separation comprises 1) flash drying, spray drying, fluid bed drying, or mechanically agitated drying, 2) gas/solid separation, and 3) cooling.

5. The process of claim 1 wherein isolating the volatile compound from the vapor product of step (c) is by condensing, distilling, adsorption, or selective scrubbing.

6. The process of claim 5 further comprising recovering all or part of the stripping agent at step (d) and recycling the stripping agent at least once to step (b), optionally reconditioning the recovered stripping agent by heating, physical reconditioning, or chemical reconditioning.

7. The process of claim 6 wherein the stripping agent is a combustion product.

8. The process of claims 1, 4, or 5 wherein the volatile compound comprises at least one of a carboxylic acid, a dicarboxylic acid, a hydroxy carboxylic acid, an ester of carboxylic acid, a monoester of dicarboxylic acid, a diester of dicarboxylic acid, a polyol, 1,3-propanediol, glycerol, ethylene glycol, 1,2-propanediol, or neopentyl glycol.

9. The process of claim 8 wherein the aqueous solution is obtained from aircraft deicing operations, antifreeze recycling operations, microemulsion cleaning solution recovery, microbial fermentation, ethanol fermentation, plant or animal material processing, or chemical synthesis.

10. A process for recovering 1,3-propanediol or glycerol from solids present in a fermentation broth comprising:
    (a) optionally pretreating the fermentation by adding $CaCO_3$ and evaporating, or adding disodium phosphate and concentrating;
    (b) mixing nitrogen with the fermentation broth;
    (c) separating 1,3-propanediol or glycerol from the solids in the fermentation broth by spray drying and filtering, fluid bed drying and cyclone separating, flash drying and cyclone separating, or mechanically agitated drying and filtering; and
    (d) isolating 1,3-propanediol or glycerol from the vapor fraction of the product of step (c) by condensing or distilling.

11. A process for recovering 1,2-propanediol or ethylene glycol from solids present in an aqueous solution comprising:
    (a) optionally pretreating the aqueous solution;
    (b) mixing nitrogen with the aqueous solution;
    (c) separating 1,2-propanediol or ethylene glycol from the solids of the aqueous solution by mechanically agitated drying and filtration; and
    (d) optionally isolating 1,2-propanediol or ethylene glycol from the vapor product of step (c) by condensing or distilling.

12. A procss for recovering dimethyl esters from solids present in an aqueous microemulsion cleaning solution comprising:
    (a) optionally pretreating the aqueous solution;
    (b) mixing nitrogen with the aqueous solution;
    (c) separating dimethyl esters from the solids of the aqueous solution by mechanically agitated drying and filtering;
    (d) optionally separating dimethyl esters from the vapor product of step (c) by condensing or distilling.

* * * * *